United States Patent [19]

Idriss

[11] Patent Number: 5,045,064
[45] Date of Patent: Sep. 3, 1991

[54] CONSTANT PRESSURE IMPLANTABLE PUMP RESERVOIR

[75] Inventor: Samir F. Idriss, Hyde Park, Mass.
[73] Assignee: Infusaid, Inc., Norwood, Mass.
[21] Appl. No.: 531,592
[22] Filed: Jun. 1, 1990
[51] Int. Cl.$^5$ .............................................. A61M 37/00
[52] U.S. Cl. ............................ 604/132; 128/DIG. 12
[58] Field of Search ............... 604/132, 133, 141, 153; 128/DIG. 12; 222/312, 315

[56] References Cited

U.S. PATENT DOCUMENTS

| | | | |
|---|---|---|---|
| 3,677,444 | 8/1972 | Merrill | 604/132 |
| 4,692,151 | 9/1987 | Blackman | 604/132 |
| 4,820,273 | 4/1989 | Reinicke | 128/DIG. 12 |
| 4,904,239 | 2/1990 | Winchall et al. | 604/132 |
| 4,909,790 | 3/1990 | Tsujikawa et al. | 604/132 |
| 4,915,693 | 4/1990 | Hassel | 604/132 |
| 4,969,873 | 11/1990 | Steinbach et al. | 128/DIG. 12 |

*Primary Examiner*—Paul J. Hirsch
*Attorney, Agent, or Firm*—Sughrue, Mion, Zinn, Macpeak & Seas

[57] ABSTRACT

An implantable device uses shape memory alloy (SMA) as the driver to compress a reservoir thereby providing a constant pressure source fluid delivery device. The SMA may form either the reservoir itself by appropriate shaped sheets or it may form bands around a flexible reservoir member. The reservoir may also be formed of rigid members pivoted or clamped using SMA actuators to bias the rigid members together.

20 Claims, 5 Drawing Sheets

CONSTANT PRESSURE IMPLANTABLE PUMP RESERVOIR

BACKGROUND OF THE INVENTION

This invention deals with implantable pumps and in particular an improvement in implantable pump reservoir technology.

Within the art there are a variety of medical devices, implanted in living bodies, used for the purpose of dispensing at very low flow rates medication from a reservoir to a remote site. Typical of such commercial products are the INFUSAID Models 100 and 400 devices. These devices employ a two-phase fluorocarbon as a constant pressure driving media for purposes of delivering the medication from the pump reservoir to the delivery site.

The technology of constructing such fluorocarbon based two-phase pump reservoirs is well known. Representative in the art are U.S. Pat. Nos. 3,731,681, 4,525,165, 4,626,244 and 4,838,887. Those patents are representative of a host of systems known in the art which all utilize a fluorocarbon fluid such as FREON (Trademark-DuPont) which is hermetically sealed between a metallic housing and a flexible bellows or diaphragm. The material of choice for the housing and diaphragm is titanium. A variable volume space is thus defined opposite the fluorocarbon and constitutes a pressurized drug reservoir.

This reservoir is connected to a flow control device such as capillary tube, peristaltic pump, positive displacement pump, valve/accumulator/valve assembly or other fluid metering device employed in such implantable pump systems.

In use, the device is placed in a body cavity and thus heated by internal heat. The liquid/vapor equilibrium of the fluorocarbon forces drug from the reservoir through the metering system at a rate which is proportional to or relatively independent from the pressure difference across the system. For example, flow through a capillary tube restrictor depends on this pressure differential whereas flow through a valve/accumulator/valve assembly does not. The output of the metering system is fed through a delivery path for infusion at a specific implant site.

The pump is generally refilled by the use of a septum causing the bellows or diaphragm to deflect and thus essentially recharge the driving fluid by recondensation of the fluorocarbon vapor.

These devices in actual commercial use have proven to be both reliable in construction and operation. One disadvantage, however, is that the liquid/vapor pump is typically affected by the fluorocarbon pressure's extreme sensitivity to body temperature. Additionally, the vapor propellent system is configured to physically isolate the movable surface of the drug reservoir thus constraining the reservoir pressure to be independent of ambient conditions. The reservoir pressures in such implantable pumps are thus "absolute" rather than "gauge". Such pumps are unable to compensate for changes in fluid pressure at the delivery site. This is a problem when a capillary tube is employed to measure the fluid. Flow rates through such long capillaries may vary by as much as 40% as a function of temperature and atmospheric pressure changes. Such variations in flow rate are well documented in the literature. For example. U.S. Pat. No. 4,299,220 defines an accumulator/regulator arrangement in conjunction with a constant flow reservoir to compensate for variations in pressure and temperature.

Moreover, such systems are relatively expensive to construct. Not only is the cost of titanium very high, but the techniques required to hermetically seal the bellows/housing assembly make such pumps very expensive alternatives to other techniques of drug delivery.

One solution to these known deficiencies in prior art systems is set forth in U.S. Pat. No. 4,772,263. In accordance with the '263 patent, an implantable pump integrates the energy storage of a mechanical spring element with the pressure compensating capabilities of a movable reservoir surface. Consequently, a single element acts as a spring driven reservoir. Such a device maintains constant flow rate performance independent of temperature fluctuations and changes in atmospheric pressure.

However, one aspect of this system is that the volume of the spring material required to store pump energy be high with respect to the volume of infusate pumped. This requirement exists in such a system because the energy must be completely stored within the spring material and only a small fraction of the material can actually be used in a mechanically reversible manner (e.g., for metals) or the energy storage per unit volume is low (e.g., for elastomers). Such an inherent limitation in system design limits the design of an implantable pump system which requires minimal size yet at the same time maximum efficiency of the device volume.

SUMMARY OF THE INVENTION

Given the deficiencies of the prior art, it is an object of this invention to define an implantable pump reservoir which is insensitive to variations in body temperature yet self compensating for changes in atmospheric pressure.

Another object of this invention is to define an implantable pump reservoir that is volumetrically efficient by providing maximum reservoir volume as a function of total device volume.

Yet another object of this invention is to provide for an implantable pump reservoir that is low in cost and easily manufactured. These and other objects of this invention are provided by utilizing a shape memory alloy (SMA) which is used to drive the reservoir. This material is a stressed metallic component which acts as a pressure source in conjunction with a movable surface that is exposed to internal body pressures. By the use of SMA, improved flow rate performance occurs yet at the same time manufacturing costs are lowered (given the fact that a liquid/vapor component is not required). The volumetric efficiency of this invention is improved when compared to that of spring driven systems.

In one embodiment of this invention, the reservoir itself is constructed of two shells of SMA with the shells expanding to dislocate the alloy when the reservoir is filled, thus pressurizing the reservoir to a constant value. Body heating maintains the alloy at a lower but constant state of stress, causing the device to operate in a reversible constant force regime.

In other embodiments of the invention the SMA is used as the driver by being wrapped around the exterior of a flexible housing or by clamping two rigid members into compression.

These and other embodiments of this invention will be defined in greater detail by referring to the attached drawing and the description of the preferred embodiments that follow.

DESCRIPTION OF THE PREFERRED EMBODIMENTS

Figure 1A:
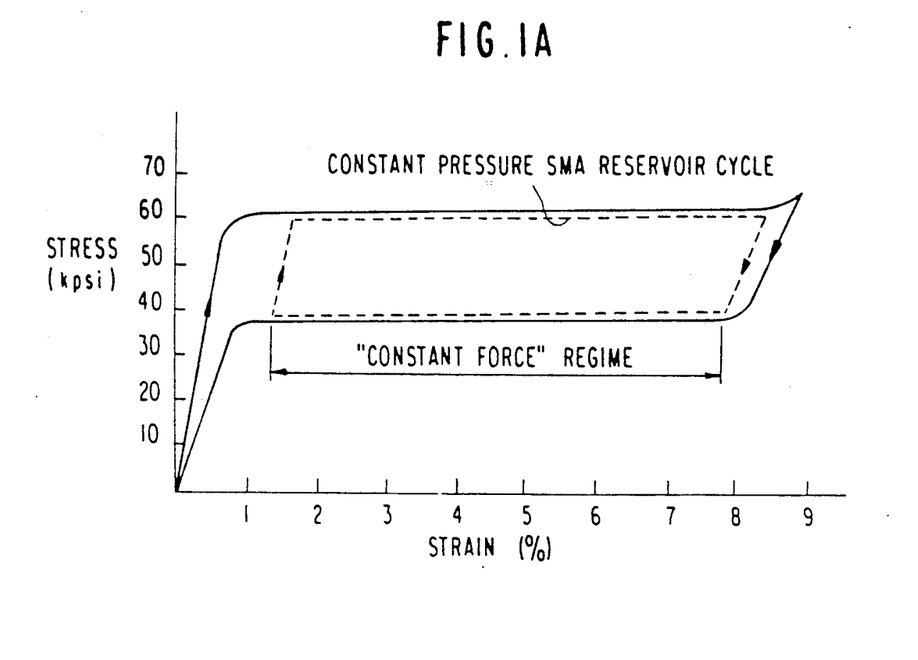
FIG. 1A is a stress strain curve for a titanium/nickel shape memory alloy undergoing superelastic behavior.
Figure 1B:
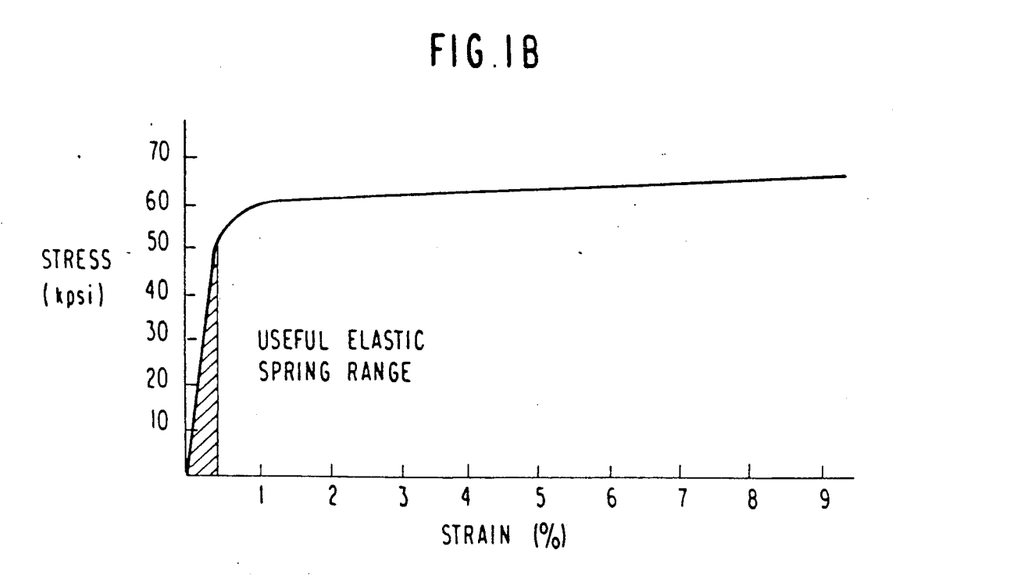
FIG. 1B is a typical stress strain curve for commercially pure titanium.

Referring to FIGS. 1A and 1B, the characteristics of the shape memory alloy (hereinafter "SMA") of this invention will be described. This invention employs SMA as either the reservoir itself or the driving mechanism for a flexible body which forms the reservoir. The SMA improves flow rate performance yet at the same time lowers manufacturing costs when compared with prior art systems which utilize a liquid/vapor system. Moreover, the use of SMA increases the volumetric efficiency of such devices when compared to prior art spring driven systems.

This is achieved by utilizing a stressed SMA component as the pressure source either in conjunction with or as a movable surface exposed to internal body pressure.

As used herein, SMA describes various types of metallic alloys which exhibit an austenite to "twinned" martensite phase change. This material is commercially available. The alloy is cooled from a high temperature through a specific transition value known as the TTR to a lower temperature state. Certain titanium/nickel, gold/cadmium and copper/zinc alloys display these properties. The twinned martensite phase has the unique property that it can be reversibly altered by shifting the symmetric, twinned crystal orientation in either direction to one of two equally stable configurations. This shift has associated with it a constant state of mechanical stress and a relatively large amount of mechanical strain. In the case of Ti/Ni alloys this strain can be as high as 8.5%. This is relatively large when compared to the elastic properties of the alloy materials.

The preferred SMA for implant use would be of the titanium/nickel (Ti/Ni) variety. These alloys contain an approximately equiatomic mixture of titanium and nickel where the TTR is adjusted by minute changes in alloy composition (typically 55-60% nickel is useful for implant) or by addition of small amounts of cobalt. Most commonly used in the aerospace industry, these alloys are manufactured in a variety of forms for example, from the Raychem Corporation of California and Furukawa in Japan. Reference is made to Hodgson, "Using Shape Memory Alloys", Shape Memory Applications, Inc, 1988, which describes the characteristics of these materials and Castleman et al, "The Biocompatibility of Nitinol" in *Biocomoatibility of Clinical Implant Materials*, CRC Press, 1981, Vol. I pp. 129-154.

Within a specific temperature range of the austenite, the deformable martensite can be induced by applying stress to the alloy, forcing it to undergo large strains at a relatively constant stress. The applied stress effectively raises the TTR, thereby stabilizing the alloy in favor of the martensite. As the stress is relieved, the structure returns to the original austenite along a somewhat lower but constant stress path with a correspondingly large strain.

FIG. 1A presents a stress vs. strain plot of Ti/Ni SMA which undergoes superelastic behavior. The constant pressure SMA reservoir cycle is set forth in dotted lines within the constant force region of the stress-strain envelope.

As illustrated in FIG. 1A, the phenomenon is known as superelastic behavior. This term "superelastic" actually refers to a thermodynamic process in which energy is transferred between the material and its ambient environment. In the case of this invention, the ambient environment is the human body which is an excellent source of relatively constant temperature, thereby stabilizing the alloy and through it, supplying the necessary energy to restore the martensite to austenite.

The operation of SMA is thus reversible as in the case of the liquid/vapor phase equilibrium system of the prior art. The stress inducement of the martensite is therefore equivalent to the recondensation of the Freon vapor during refill. That is, the temperature induced return to austenite is similar to the reheating/re-vaporization of the prior art Freon during discharge. Other than this analog, in terms of reversibility of operation the systems are, as will be demonstrated, materially different.

By referring to FIGS. 1A and 1B, it can be appreciated that use of the SMA inherently differs from the use of a metallic or elastomeric spring. A spring element operates following Hooke's Law. It displays elastic stress which is linerally proportional to strain. In FIG. 1B a stress-strain curve illustrates that the performance of a titanium wire stressed in tension is similar to that of a spring which follows Hooke's Law. Hooke's Law provides that the elastic force in a spring is proportional to the extension of that spring. Similarly, in the titanium's elastic range, the stress is proportional to the strain. However, a spring has no phase change or no appreciable heat transfer associated with it. Thus, its performance is not the result of any thermodynamic change of state. Rather, the spring stores its energy internally whereas the SMA must operate in a thermally conductive environment. In accordance with this invention, body heat actually does the work to pressurize the SMA reservoir. This, coupled with the fact that 8.5% of the length of a SMA can be utilized, allows for an extremely volumetric efficient system. The majority of the energy used to pressurize the reservoir is thus not stored in the SMA but rather is supplied by the body and transformed by the alloy into useful mechanical work.

By Referring to FIGS. 1A and 1B the constant pressure cycle of a SMA device is compared to the use of commercially pure titanium operated as a spring. FIG.

1B illustrates that the elastic stress range of titanium for use as a spring resides in a very narrow strain band. In contrast, the SMA material operates over a relatively long strain percentage in a fairly narrow stress regime.

Figures 2A, 2B, 3B:
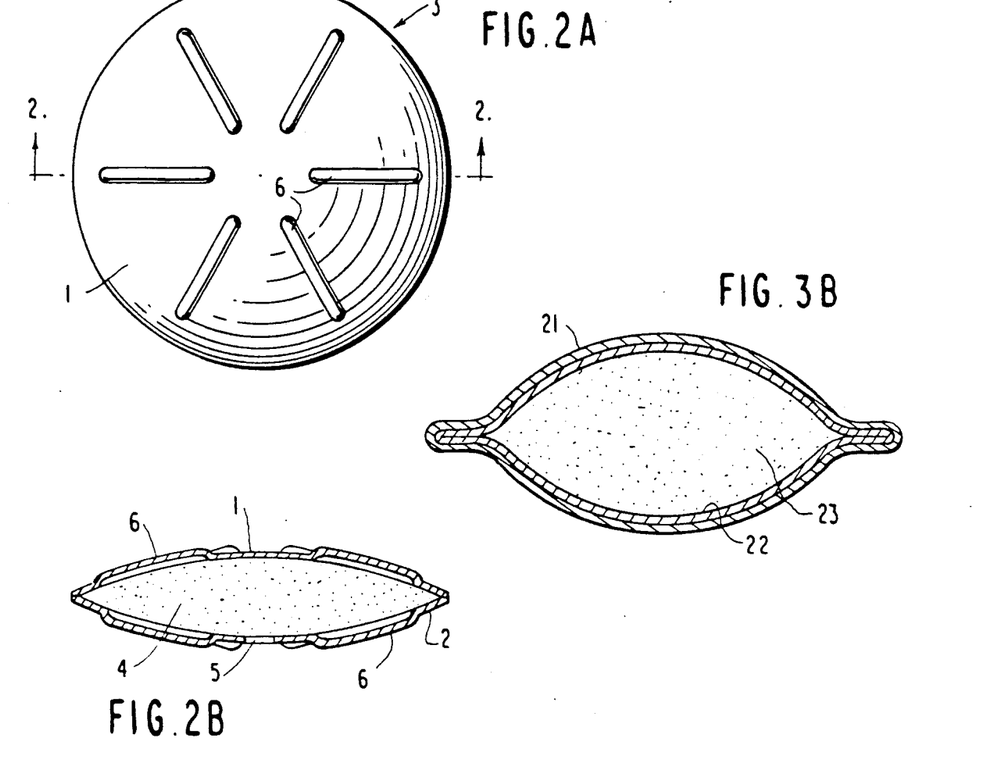
FIG. 2A is the top view of a first preferred embodiment of this invention.
FIG. 2B is a sectional view taken along section line 2—2 in FIG. 2A.
FIG. 3B is a sectional view along section line 3—3 in FIG. 3A.

Referring now to FIGS. 2A and 2B, the first embodiment of this invention is depicted. In accordance with this invention, the reservoir is constructed utilizing two shells with SMA illustrated as elements 1 and 2 in FIG. 2B. The two shells are joined at their respective perimeters to form a sealed reservoir 3 having an internal infusate cavity 4. A flow passage 5 is defined between the reservoir 4 to provide access thereto.

In order to minimize the reservoir volume change due to the initial elastic deformation of the alloy (and thereby force the reservoir to operate in a regime of constant pressure). the shell elements 1 and 2 are designed with stiffening embossments 6 to increase their internal flexural stresses to the "superelastic", constant force regime during flexure. Alternatively, the thickness of the shell elements 1 and 2 can be increased and/or the shell elements preformed in concave inward shapes to allow a residual stress state to exist in the shells after assembly.

When the reservoir 3 is filled via the flow passage 5, the two SMA shells 1 and 2 distend in a similar manner, further dislocating the alloy. As noted, this dislocation occurs at a constant stress thereby pressurizing the reservoir to a constant pressure value. Following distention, heat from the human body maintains the alloy at a somewhat lower but constant state of stress, thereby pressurizing the infusate cavity 4.

In the embodiment of FIG. 2, only two elements are required, joined together to form the reservoir itself. By proper geometry of the SMA shells, the amount of infusate that will maintain the alloy within its constant stress regime can be determined.

Figure 3A:
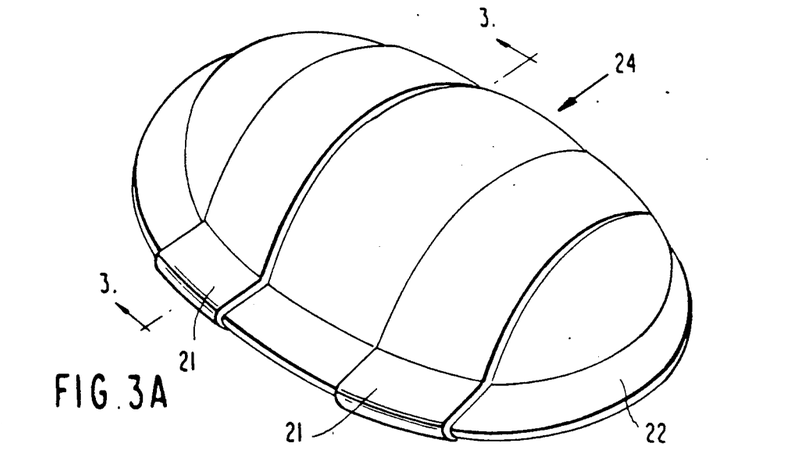
FIG. 3A is a schematic perspective view of a second preferred embodiment of this invention.

A second embodiment of this invention is illustrated in FIGS. 3A and 3B. In this embodiment SMA is used as a driver to pressurize another component which defines a flexible housing. As illustrated in FIG. 3A, two bands of SMA 21 are wrapped around the exterior of a flexible housing 22. The housing itself forms the infusate storage cavity 23 as illustrated in FIG. 3B.

As the infusate fills this cavity 23, the housing 22 expands against the bands 21. The bands are thus stretched to apply a constant level of tension to the housing 22 which results in a constant infusate pressure in the infusate cavity 23. The arrow 24 illustrates the point where a flow passage may be defined in the flexible housing 22.

Figure 4A:
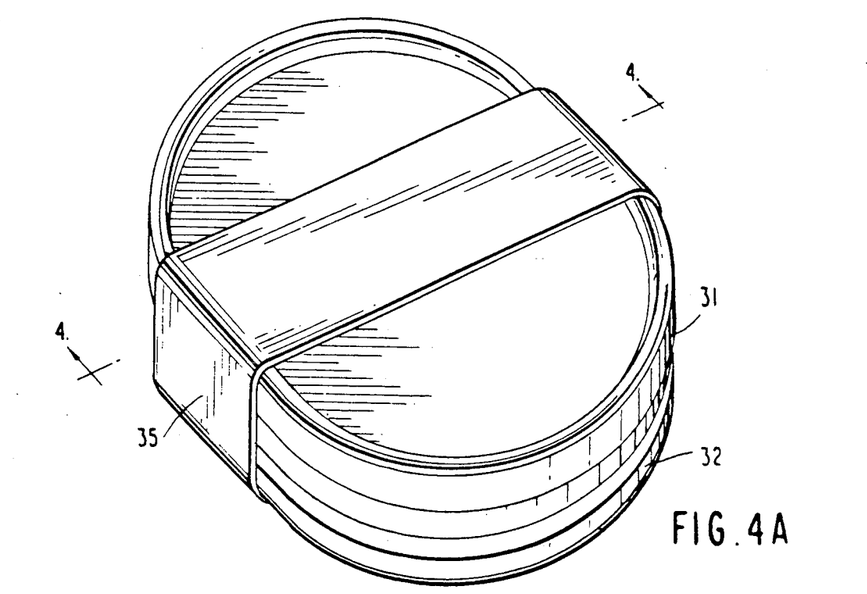
FIG. 4A is a perspective view of a third preferred embodiment of this invention.
Figure 4B:
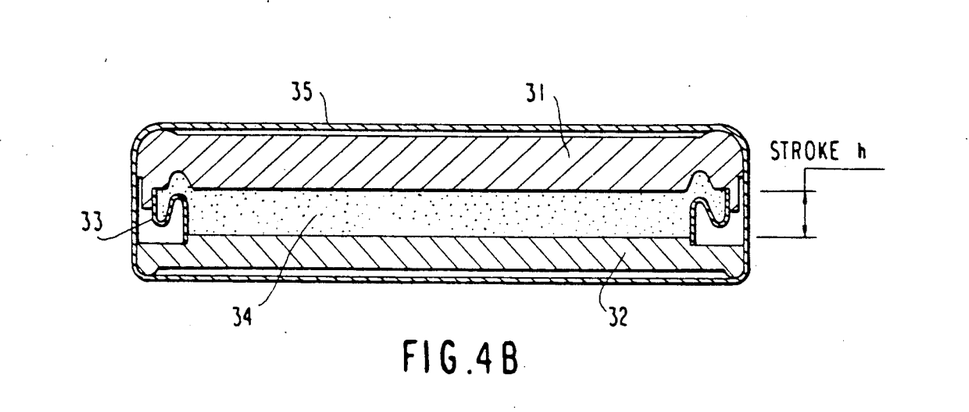
FIG. 4B is a sectional view along line 4—4 of FIG. 4A.

A third embodiment of this invention is illustrated in FIGS. 4A and 4B. This embodiment differs from the first two in that it employs a rigid housing 31 which is combined with a rigid movable wall 32. The two walls 31 and 32 are joined together by means of an annular flexible seal 33. The region formed therebetween is the fluid cavity 34.

A continuous SMA band 35 circles the housing and wall. Tension in the SMA band 35 forces the wall 32 upward toward the housing 31. This compression defines a stroke "h" as illustrated in FIG. 4B. The reduction in volume of the cavity 34 pressurizes the fluid therein.

If the surface area of the wall 32 is designated as A, and the magnitude of the tensile force in the band is designated as T, then the differential pressure P generated in the reservoir can be given as: $P = 2T/A$, where $P = Pr - Pa$. Pr is the absolute pressure in the reservoir and Pa is the ambient pressure acting on the wall, housing and catheter exit.

It will be appreciated that for a fixed wall area the differential pressure thus depends solely on the band tension T and is independent of ambient pressure.

As illustrated in FIG. 4A, the correct length of the SMA band can be ascertained so that the total strain of the band can be made to fit within the constant stress regime of the SMA stress-strain curve. The total cross-sectional area of the band can then be selected to provide the necessary force to the drug reservoir 34.

For instance, if the total reservoir volume is defined as V, then the required stroke "h" of the movable wall is: $h = V/A$. Assuming, for example, that the SMA constant force regime has a width of 5% strain, the required working perimeter L of the SMA band is defined by $L = 2h/0.05$.

Figure 5A:
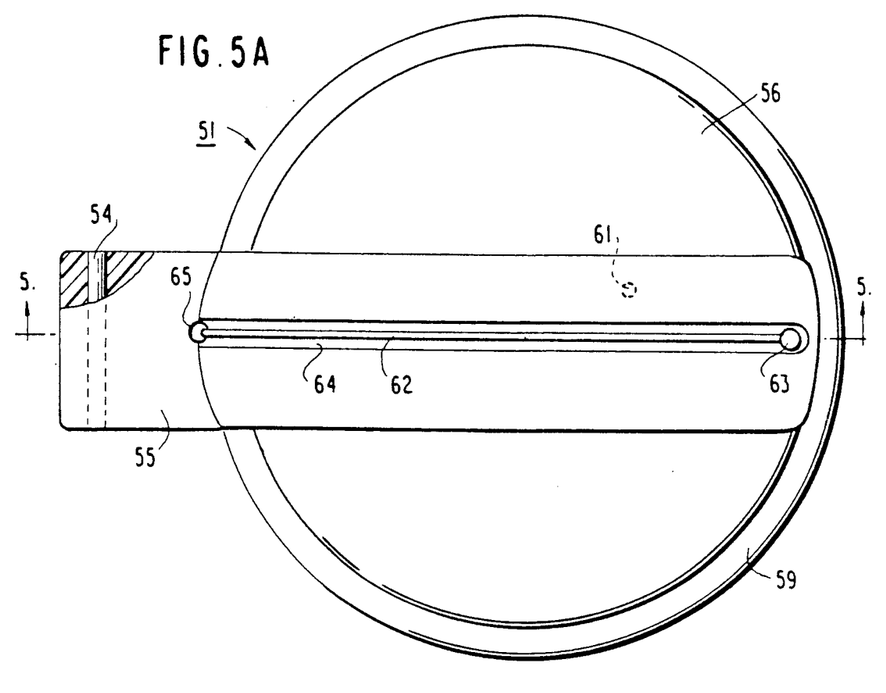
FIG. 5A is a partial top view of a fourth preferred embodiment of this invention.
Figure 5B:
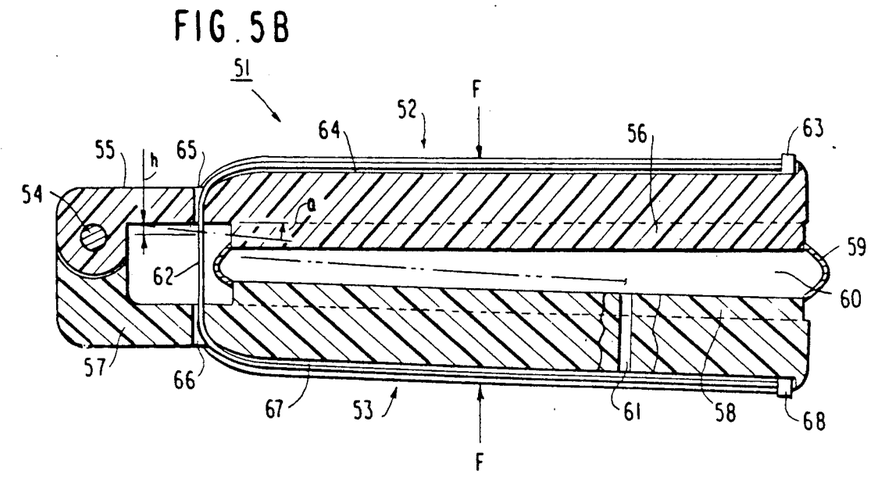
FIG. 5B is a cut-away view along line 5—5 of FIG. 5A.

Referring now to FIGS. 5A and 5B, a fourth preferred embodiment of this invention is depicted. This embodiment employs a pivoted lever assembly to create a constant pressure in the infusate chamber. As illustrated in FIG. 5B, the clamshell-like reservoir 51 has an upper housing 52 coupled to a lower housing 53 by means of a pivot 54. The upper housing 52 has a rigid lever arm 55 which is integrally connected to a pressure plate 56 having a fluid surface area A. This area is determined geometrically normal to the travel of the plate.

The lower housing 53 comprises a rigid lever arm 57 integrally connected to an identical lower pressure plate 58. Both pressure plates 56 and 58 are joined by a circumferential flexible seal 59. This forms the contained infusate cavity 60. A fluid port 61 is provided in the lower pressure plate 58 to permit fluid communication with the cavity 60.

The SMA wire 62 is attached to an upper pin 63 located on an upper lever arm 55. The location of the SMA wire 62 is thus positioned remote from the pivot 54. The wire 62 is pulled in tension over a curvilinear channel surface 64. It then passes through the upper pilot hole 65. The wire 62 continues to a similar pilot hole 66 in the lower lever arm 57 and then over a similar curvilinear channel surface 67 to a lower mounting pin 68.

The housings 52 and 53 are constructed from a material (such as Teflon) having a low coefficient of friction with respect to the SMA wire 62 as it passes over the curvilinear surfaces 64 and 67. Therefore, the tension in the wire 62 is applied to the pressure housings 52 and 53 along the surfaces 64 and 67. It is transmitted to the pressure plates 56 and 58 through the lever arms 55 and 57 in conjunction with the pivot 54. The resulting force F as illustrated by the arrow in FIG. 5B is applied to the plate surface having an area A and generates a fluid pressure P in the infusate cavity 60 such that $P = F/A$.

In operation, when the infusate cavity 60 is filled, the included angle "a" between the lever arms 55 and 57 increases. This is illustrated in FIG. 5B. The increased angle thus stretches the SMA wire 62 between the pilot holes 65 and 66. This occurs because of the distance increasing between the two pilot holes. Given the low frictional elements, this increase in distance is distributed to the entire SMA wire 62 as tension is maintained by the terminal mounting pins 63 and 68. The change in distance "h" is small with respect to the total length "L" of the wire 62. Consequently, the mechanical strain on the SMA wire 62 is small and the wire can be used in the constant stress that is, superelastic region to effectuate a constant pressure P in the infusate cavity 60.

As an example, if the total strain of the wire 62 is defined by h/L, where L is the initial length of the wire 62, the total strain must be less than 0.05 to allow the alloy to operate in the constant stress regime. It will be recognized that L must be equal to or greater than h/0.05. Such can be achieved by correct sizing of the lever arms 55 and 57.

Referring now to FIG. 6, a schematic view of a complete system is illustrated. Such a complete system includes a reservoir 41 having an outlet flow passage 42. A refill septum 43 is defined in the reservoir to allow refilling of infusate. A bacterial filter 44 is located in the outlet flow path which includes a flow conduit 45.

In accordance with this invention, any number of flow metering devices can be used in the flow path. Those flow metering devices are illustrated schematically by the dotted line box 46. As illustrated in FIG. 6B, one flow metering device may be a capillary tube 47 which forms a flow restrictor.

Figure 6A:
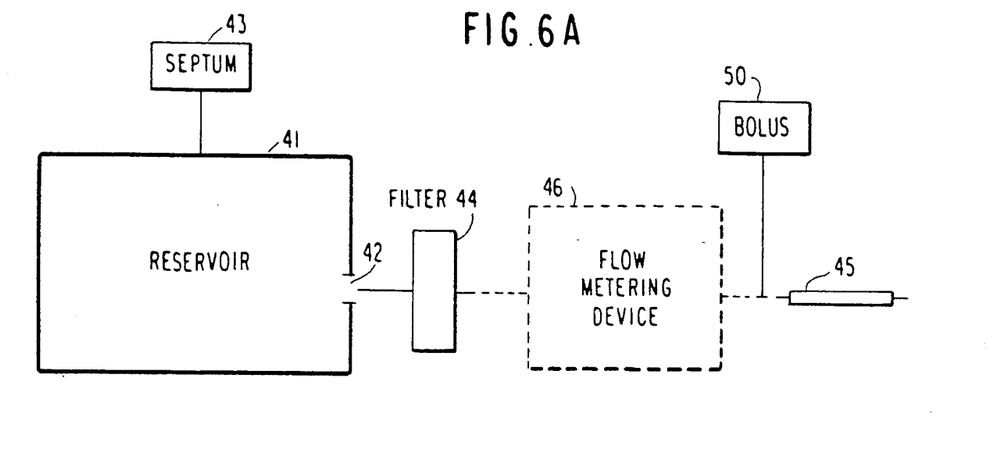
FIGS. 6a-6d is a schematic view illustrating a complete system of this invention including various attachments which may be employed.
Figure 6B:
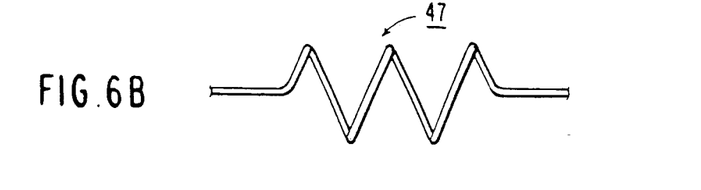
Figure 6C:
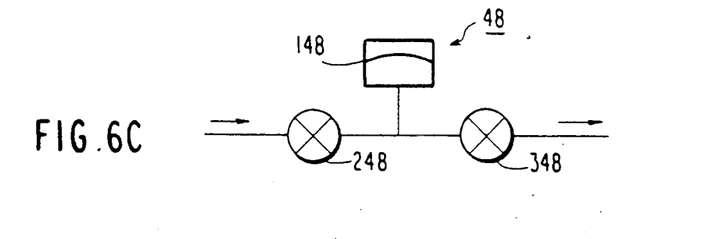

Alternatively, a valve/accumulator/valve assembly 48 can be used, as illustrated in FIG. 6C. That is, interposed between a pair of valves 248 and 348 is an accumulator 148. The valve 248 opens to allow fluid into the accumulator cavity 148. That valve is then closed and the outlet valve 348 is opened to allow fluid accurately accumulated to a metered level to be output, producing a volumetric output pulse in the system. Such valve/accumulator/valve assembles are recognized in the art, for example, in U.S. Pat. No. 4,838,887.

Figure 6D:
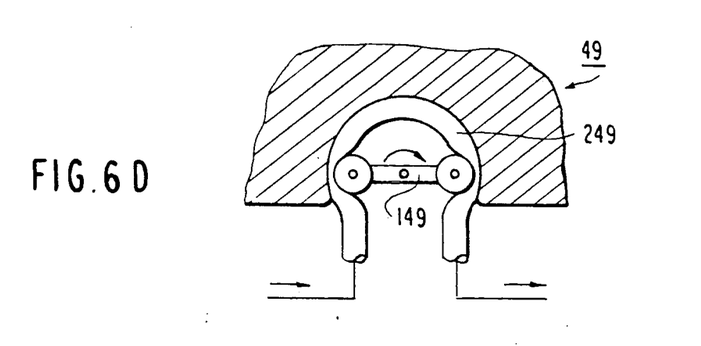

Alternatively, a peristaltic pump 49 can be used as illustrated in FIG. 6D. Such a pump employs a rotating arm assembly 149 which constricts a tube 249 thereby creating a peristaltic action in the system.

Also, an auxiliary bolus chamber 50 can be added to the flow path as illustrated in FIG. 6A.

An advantage of this invention is that given the temperature dependence of the SMA, refilling the reservoir is accomplished more easily than in the prior art. Prior to this invention pressure equivalent to the pumping pressure had to be applied to refill with infusate. With this invention, by either localized cooling of the pump or cooling of the drug, the pressure required is reduced because the SMA will relax at temperatures below the TTR. Thus the time to refill and inconvenience to the patient are both reduced.

While illustrated in the preferred embodiment of this invention, it is apparent that modifications of this invention can be practiced. For example, other shape memory alloys and housing configurations can be selected. Multiple bands can be used to increase force. The bands can be rerouted to increase band length. Alternatively. SMA component configurations such as torsion elements, cantilever elements, pulley actuators and the like can be employed. Additionally, intermediate force conducting elements such as flexible cables, rigid lever arms or cammed surfaces can be used to isolate the SMA or to conduct force to the movable housing or wall without deviating from the scope of this invention. Other modifications can also be practiced.

Having now described my invention, I claim:

1. An implantable pump reservoir comprising:
   a housing having an internal chamber of variable volume, at least a deformable shape memory alloy component to apply a contracting force reducing the volume of said housing and;
   means providing access to said chamber whereby when said chamber is filled with a material said shape memory alloy is stressed so that said material is released by the application of said contracting force.

2. The implantable device of claim 1 wherein said shape memory alloy component comprises at least one shell forming a portion of said housing.

3. The implantable device of claim 1 wherein said shape memory alloy component comprises a strap positioned on said housing to cause contraction thereof.

4. The implantable device of claim 3 wherein said housing comprises a flexible media and said shape memory alloy strap is disposed around said flexible media.

5. The implantable device of claim 3 wherein said housing comprises a pair of spaced rigid plates coupled together by a flexible member and said strap comprises a belt biasing said rigid plates in compression.

6. The implantable pump of claim 3 wherein said housing comprises first and second members hinged together, means defining a seal between said first and second member, and said strap comprises a wire having ends anchored to both of said members to cause one of said members to move relative to the other and reducing the distance therebetween.

7. The implantable device of claim 1 wherein said means providing access to said chamber, comprises a self-sealing refill port in fluid communication with said chamber.

8. The implantable device of claim 1 further comprising a flow regulation means coupled to said means providing access to said chamber, and said means for providing access comprises an outlet port and filter.

9. The implantable device of claim 1 wherein said shape memory alloy comprises titanium/nickel and said component comprises a strip of said titanium/nickel having a length sufficient to provide a pumping stroke for expansion and contraction of said chamber based on superelastic stressing of said alloy.

10. An implantable device as in claim 1 further comprising an outlet catheter coupled to said housing.

11. An implantable drug infusion system comprising;
    a housing including a shape memory alloy to apply a contractive force,
    a variable volume chamber within said housing, and means establishing fluid communication to said chamber, wherein as said chamber is filled with a drug to be infused and said shape memory alloy is stressed to provide a relatively constant compressive force to said housing thereby reducing the volume of said chamber and expelling said drug.

12. The implantable device of claim 11 wherein said shape memory alloy comprises at least one shell forming said housing.

13. The implantable device of claim 11 wherein said shape memory alloy comprises a strap positioned on said housing and movable therewith.

14. The implantable device of claim 13 wherein said housing comprises a flexible member, said shape memory alloy strap disposed around said flexible member.

15. The implantable device of claim 13 wherein said housing comprises a pair of spaced rigid plates coupled together by a flexible member and said strap joins said rigid plates together in compression.

16. The implantable pump of claim 13 wherein said housing comprises first and second members hinged together, means defining a seal between said first and second members, and said strap comprises a wire having ends fixed to both of said members to cause one of said members to move relative to the other and reducing the distance therebetween.

17. The implantable device of claim 11 wherein said means establishing fluid communication comprises a refill septum.

18. The implantable device of claim 11 wherein said means establishing fluid communication comprises an outlet having a filter.

19. The implantable device of claim 17 further comprising flow regulation means coupled to said outlet.

20. The implantable device of claim 11 wherein said shape memory alloy comprises titanium/nickel.

* * * * *